US006960662B2

(12) United States Patent
Beylin et al.

(10) Patent No.: US 6,960,662 B2
(45) Date of Patent: Nov. 1, 2005

(54) PROCESS FOR PREPARING 2-(4-PYRIDYL) AMINO-6-DIALKYLOXYPHENYL-PYRIDO[2, 3-D]PYRIMIDIN-7-ONES

(75) Inventors: Vladimir Genukh Beylin, Ann Arbor, MI (US); Richard Jungkyu Lee, Holland, MI (US); Mark Eugene Marlatt, Grass Lake, MI (US)

(73) Assignee: Warner-Lambert Company, Ann Arbor, MI (US)

( * ) Notice: Subject to any disclaimer, the term of this patent is extended or adjusted under 35 U.S.C. 154(b) by 0 days.

(21) Appl. No.: 10/343,805

(22) PCT Filed: Jul. 12, 2001

(86) PCT No.: PCT/US01/22001

§ 371 (c)(1),
(2), (4) Date: Feb. 4, 2003

(87) PCT Pub. No.: WO02/12237

PCT Pub. Date: Feb. 14, 2002

(65) Prior Publication Data

US 2003/0216415 A1 Nov. 20, 2003

Related U.S. Application Data

(60) Provisional application No. 60/223,084, filed on Aug. 4, 2000.

(51) Int. Cl.$^7$ .................... C07D 471/04; C07D 519/00; C07D 239/46
(52) U.S. Cl. ...................... 544/279; 544/317
(58) Field of Search .......................... 544/279

(56) References Cited

U.S. PATENT DOCUMENTS

| 5,525,724 | A |   | 6/1996 | Hunds |            |
|-----------|---|---|--------|-------|------------|
| 5,733,914 | A |   | 3/1998 | Blankley et al. | |
| 5,801,183 | A |   | 9/1998 | Keana et al. | |
| 5,945,422 | A | * | 8/1999 | Doherty et al. | 514/264.11 |
| 2003/0149001 | A1 | * | 8/2003 | Barvian et al. | 544/279 |
| 2003/0176700 | A1 | * | 9/2003 | Tjiong et al. | 544/279 |
| 2003/0220345 | A1 | * | 11/2003 | Hamby et al. | 544/279 |

FOREIGN PATENT DOCUMENTS

| EP | 0305184 A1 | 8/1988 |
| WO | WO 96/22990 A2 | 8/1996 |
| WO | WO 96/34867 A1 | 11/1996 |
| WO | WO 99/47525 A1 | 9/1999 |
| WO | WO 99/50263 A1 | 10/1999 |

OTHER PUBLICATIONS

Chemical Abstracts abstract for E. Peters, et al., "Synthesis of some 2,4,5–trisbstituted pyrimidines" J. Org. Chem, 1960, pp 2137–2142, vol. 25.

D. H. Boschelli, et al., "Snthesis and Tyrosine Kinase Inhibotory Activity of a Series of 2–Amino–8H–pyrido[2, 3–d]pyrimidines: Identification of Petent, Selective Platelet–Derived Growth Factor Receptor Tyrosine Kinase Inhibitors", J. Med. Chem, 1998, pp 4365–4377, vol. 41.

S. R. Klutchko, et al., "2–Substituted Aminopyrido[2,3–d] pyrimidin–7(8H)–ones. Structure–Activity Relationships Against Selected Tyrosine Kinases and in Vitro and in Vivo Anticancer Activity", J. Med. Chem., 1998, pp 3276–3292, vol. 41.

* cited by examiner

Primary Examiner—Mark L. Berch
(74) Attorney, Agent, or Firm—John H. Engelmann; Steven R. Eck; Charles Ashbrook

(57) ABSTRACT

The present invention relates to a process for preparing 2-(pyridin-4-ylamino-pyrido [2,3-d]pyrimidine of Formula II

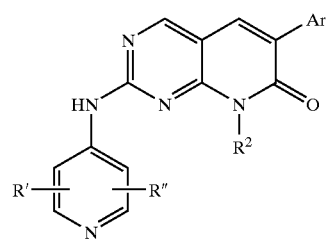

by reacting a 4-aminopyridine of the formula

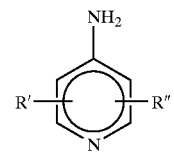

with a 2-(4-imino-4H-pyridin-1-yl)-pyrido[2,3-d] pyrimidine of Formula I

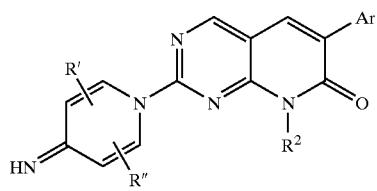

in the presence of a base. It also relates to an alternative process for preparing a compound of Formula II by reacting the aminopyridine hereinabove with

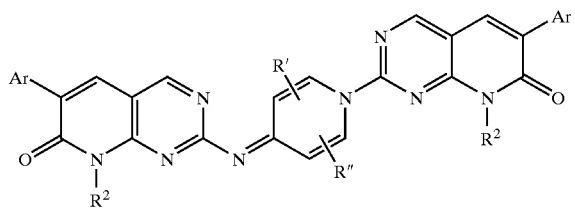

in a unreactive organic solvent. It also relates to the compound of Formula III.

9 Claims, No Drawings

PROCESS FOR PREPARING 2-(4-PYRIDYL) AMINO-6-DIALKYLOXYPHENYL-PYRIDO[2,3-D]PYRIMIDIN-7-ONES

This application is a 371 application of PCT/US01/22001 filed Jul. 12, 2001, which claims the benefit of priority to U.S. provisional application Ser. No. 60/223,084 filed Aug. 4, 2000.

FIELD OF THE INVENTION

This invention concerns a chemical process for preparing pyrido[2,3-d]pyrimidines having a pyridylamino group at the 2-position.

BACKGROUND OF THE INVENTION

U.S. Pat. No. 5,733,914 (which is incorporated herein by reference) describes a series of pyrido[2,3-d]pyrimidines that inhibit protein tyrosine kinase mediated cellular proliferation. The compounds are anti-angiogenic agents, and as such are useful for treating cancer, particularly leukemia and breast cancer. The U.S. Pat. No. 5,733,914 patent teaches that a particularly preferred group of compounds are substituted at the 2-position with an arylamino group, and that the aryl moiety can be a pyridyl group. 2-(4-Pyridyl)amino-pyrido[2,3-d]pyrimidines appear to be a preferred group of compounds because of their metabolic stability and tyrosine kinase selectivity. One such compound, namely 2-(pyridin-4-ylamino)-6-(3,5-dimethoxyphenyl)-8-ethyl-8H-pyrido[2,3-d]pyrimidin-7-one, is currently being studied as a possible clinical candidate for treating cancer.

Because these compounds are commercially viable anti-cancer agents, the need exists for a synthetic process that affords the desired compound in high purity and satisfactory yields. This invention provides a commercially viable process for making such pyridylamino-pyrido[2,3-d]pyrimidines.

SUMMARY OF THE INVENTION

This invention provides a chemical process for preparing 2-(pyridin-4-ylamino)-pyrido[2,3-d]pyrimidines comprising reacting a 4-aminopyridine with a 2-(4-imino-4H-pyridin-1-yl)-6-aryl-8-substituted-8H-pyrido[2,3-d]pyrimidine-7-one. More particularly, the invention provides a process for reacting a 4-aminopyridine of the formula

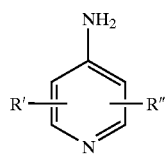

with an imine compound of the Formula I

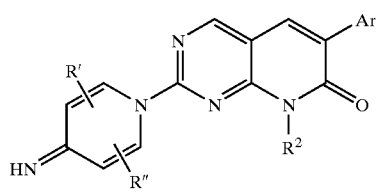

in the presence of a base to provide a pyridylamino compound of Formula II

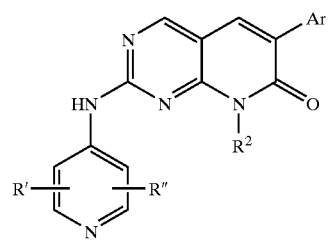

wherein:

R' and R" independently are hydrogen, $C_1$–$C_6$ alkyl, $C_1$–$C_6$ alkoxy, phenyl, or $C_1$–$C_6$ alkanoyl;

$R^2$ is $(CH_2)_n$Ph, where Ph is phenyl or substituted phenyl, and n is 0, 1, 2, or 3; heteroaromatic; cycloalkyl; $C_1$–$C_6$ alkanoyl; $C_1$–$C_6$ alkyl; $C_2$–$C_6$ alkenyl; or $C_2$–$C_6$ alkynyl, where the alkyl, alkenyl, and alkynyl groups may be substituted by $NR_5R_6$, phenyl, substituted phenyl, thioalkyl, alkoxy, carboxy, or cycloalkyl, and where $R_5$ and $R_6$ are independently $C_1$–$C_6$ alkyl; $C_2C_6$ alkenyl; $C_2$–$C_6$ alkynyl; $(CH_2)_n$Ph where Ph is phenyl or substituted phenyl, and n is 0, 1, 2, or 3; cycloalkyl; or heteroaromatic; or $R_5$ and $R_6$ taken together with the nitrogen to which they are attached can complete a ring having 3 to 7 carbon atoms and optionally containing 1, 2, or 3 heteroatoms selected from nitrogen, substituted nitrogen, oxygen, and sulfur;

Ar is phenyl, substituted phenyl, or heteroaromatic;

and the pharmaceutically acceptable salts thereof.

Preferably, R' and R" independently are hydrogen, $C_1$–$C_6$ alkyl, $C_1$–$C_6$ alkoxy, or phenyl.

It is also preferred that $R_2$ is $(CH_2)_n$Ph, where Ph is phenyl or substituted phenyl, and n is 0, 1, 2, or 3; heteroaromatic; cycloalkyl; $C_1$–$C_6$ alkyl; or $C_2$–$C_6$ alkenyl; where the alkyl and alkenyl groups may be substituted by $NR_5R_6$; phenyl; substituted phenyl; or cycloalkyl; and where $R_5$ and $R_6$ are independently $C_1$–$C_6$ alkyl; $C_2$–$C_6$ alkenyl; $(CH_2)_n$Ph where Ph is phenyl or substituted phenyl, and n is 0, 1, 2, or 3; cycloalkyl; or heteroaromatic; or $R_5$ and $R_6$ taken together with the nitrogen to which they are attached can complete a ring having 3 to 7 carbon atoms and optionally containing 1, 2, or 3 heteroatoms selected from the group consisting of nitrogen, substituted nitrogen, oxygen, and sulfur.

In a preferred embodiment, R' and R" both are hydrogen.

In another preferred embodiment, Ar is substituted phenyl and is more preferably 3,5-di-$C_1$–$C_6$ alkoxyphenyl. Ar is most preferably 3,5-dimethoxyphenyl.

In another preferred embodiment, $R^2$ is $C_1$–$C_6$ alkyl.

It is preferred that the compound of Formula II is 2-(pyridin-4-ylamino)-6-(3,5-dimethoxyphenyl)-8-ethyl-8H-pyrido[2,3-d]pyrimidin-7-one.

In a further embodiment, the invention provides a process for preparing a pyridylamino pyridopyrimidine compound of Formula II comprising reacting an aminopyridine with a dimer-like compound of Formula III

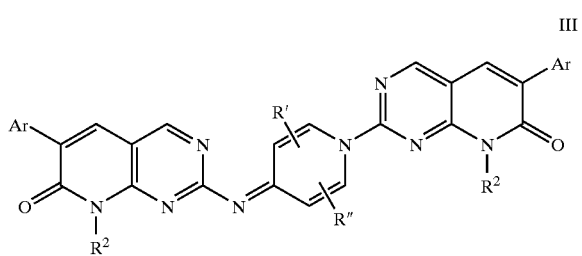

III wherein Ar, R', R", and $R^2$ are as defined above. Additionally, for a compound of Formula III, $R^2$ can be hydrogen. The process comprises reacting the dimer-like compound of Formula III with a catalytic amount of an aminopyridine of the formula

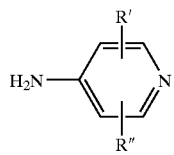

in an unreactive organic solvent. The compounds of Formula III are provided as a further embodiment of the invention. These compounds are named as 2-{4-[(6-aryl-7-oxo-8-substituted-8H-pyrido[2,3-d]-pyrimidin-2-yl)-imino]4H-pyridin-1-yl}-6-aryl-8-substituted-8H-pyrido[2,3-d]-pyrimidin-7-ones.

Also provided by this invention are new compounds defined by Formulas I and III above. These compounds are useful as starting materials or intermediates in the synthesis of the pyridylamino pyridopyrimidine compounds of Formula II.

In still a further embodiment, the invention provides a process for preparing a 2-alkylsulfanyl pyridopyrimidine of Formula IV comprising reacting an aryl acetic acid ester with a 2-alkylsulfanyl-4-alkylamino-pyrimidine-5-carboxaldehyde according to the following scheme:

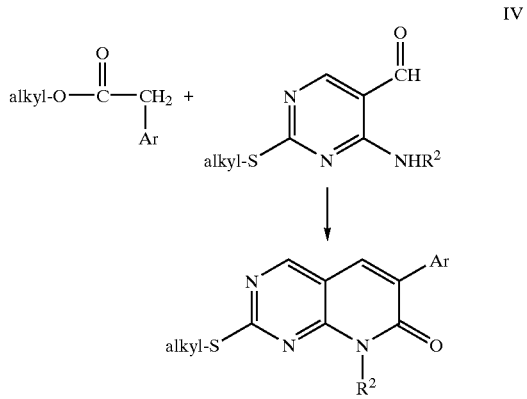

IV wherein Ar and $R^2$ are as defined above. Additionally, for a compound of Formula IV, $R^2$ can be hydrogen.

The 2-alkylsulfanyl pyridopyrimidines of Formula IV are useful as intermediates in the synthesis of 2-(4-imino-4H-pyridin-1-yl)-pyridopyrimidines of Formula I.

DETAILED DESCRIPTION OF INVENTION

For purposes of the present invention, the terms "alkyl" and "$C_1$–$C_6$ alkyl" mean a straight or branched hydrocarbon radical having from 1 to 6 carbon atoms and include, for example, methyl, ethyl, n-propyl, isopropyl, n-butyl, sec-butyl, isobutyl, tert-butyl, n-pentyl, n-hexyl, and the like. The term "$C_1$–$C_6$ alkyl" includes within its definition the term "$C_1$–$C_3$ alkyl".

"Halo" or "halogen" includes fluoro, chloro, bromo, and iodo.

The terms "alkenyl" and "$C_2$–$C_6$ alkenyl" mean a straight or branched hydrocarbon radical having from 2 to 6 carbon atoms and 1 double bond and includes ethenyl, 3-buten-1-yl, 2-ethenylbutyl, 3-hexen-1-yl, and the like.

The terms "alkynyl" and "$C_2$–$C_6$ alkynyl" mean a straight or branched hydrocarbon radical having from 2 to 6 carbon atoms and at least one triple bond. Typical $C_2$–$C_6$ alkynyl groups include propynyl, 2-butyn-1-yl, 3-pentyn-1-yl, and the like.

The terms "cycloalkyl" and "$C_3$–$C_6$ cycloalkyl" mean a cyclic hydrocarbyl group such as cyclopropyl, cyclobutyl, cyclohexyl, and cyclopentyl.

The terms "alkoxy" and "$C_1$–$C_6$ alkoxy" refer to the alkyl groups mentioned above binded through oxygen, examples of which include methoxy, ethoxy, isopropoxy, tert-butoxy, and the like.

The term "$C_1$–$C_6$ alkanoyl" refers to an alkyl group, as defined above, linked through a carbonyl, i.e., $C_1$–$C_5$ alkyl

Such groups include formyl, acetyl, propionyl, butyryl, and isobutyryl.

"Acyl" means an alkyl or aryl (Ar) group bonded through a carbonyl group

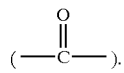

For example, acyl includes a $C_1$–$C_6$ alkanoyl, including substituted alkanoyl, wherein the alkyl portion can be substituted by $NR_5R_6$ or a carboxylic or heterocyclic group. Typical acyl groups include acetyl, benzoyl, and the like.

The alkyl, alkenyl, alkoxy, and alkynyl groups described above may be substituted. The substituent groups which may be part of the alkyl, alkenyl, alkoxy, and alkynyl groups are $NR_5R_6$, phenyl, substituted phenyl, thio($C_1$–$C_6$)alkyl, $C_1$–$C_6$ alkoxy, carboxy, $C_1$–$C_6$ alkoxycarbonyl, cycloalkyl, and a 5- to 7-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph.

Examples of substituted alkyl groups thus include 2-aminoethyl, 2-diethylaminoethyl, 2-dimethylaminopropyl, ethoxycarbonylmethyl, 3-phenylbutyl, methylsulfanylmethyl, methoxymethyl, 3-hydroxypentyl, 2-carboxybutyl, 4-chlorobutyl, 3-cyclopropylpropyl, 3-morpholinopropyl, piperazinylmethyl, and 2-(4-methylpiperazinyl)ethyl.

Examples of substituted alkenyl groups thus include 2-diethylaminoethenyl, 3-amino-2-butenyl, 3-(1-piperazinyl)-1-propenyl, 3-hydroxy-1-propenyl, 2-(1-s-triazinyl)ethenyl, 3-phenyl-3-pentenyl, and the like.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexynyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-diethylamino-3-buten-1-yl, 5-ethylmethylamino-3-pentyn-1-yl, 4-morpholinobutyl, 4-tetrahydropyridinylbutyl-3-imidazolidin-1-ylpropyl, 4-tetrahydrothiazol-3-yl-butyl, phenylmethyl, 3-chlorophenylmethyl, and the like.

The term "Ar" refers to unsubstituted and substituted aromatic and heteroaromatic groups. Heteroaromatic groups have from 4 to 9 ring atoms, from 1 to 4 of which are selected from O, S, and N. Preferred groups have 1 or 2 heteroatoms in a 5- or 6-membered aromatic ring. Mono and bicyclic ring systems are included. Typical Ar groups include phenyl, 3,5-dimethoxyphenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, and the like.

Preferred Ar groups are phenyl and phenyl substituted by 1, 2, or 3 groups independently selected from alkyl, alkoxy, alkanoyl, —CN, —NO$_2$, —COOR$_8$ (where R$^8$ is C$_1$–C$_6$ alkyl, or benzyl), —CF$_3$, and alkanoyloxy. Disubstituted phenyl is most preferred, and 3,5-disubstituted phenyl, such as 3,5-dimethoxyphenyl, is especially preferred.

Typical Ar substituted phenyl groups which are preferred thus include 2-aminophenyl, 3-chloro-4-methoxyphenyl, 2,6-dimethylphenyl, 2,6-diethylphenyl, 2-n-hexyl-3-fluorophenyl, 3-isopropoxyphenyl, 4-chloromethylphenyl, 3,4-dimethoxyphenyl, 3,5-dimethoxyphenyl, 2,6-dichlorophenyl, 4-(3-aminopropoxy)phenyl-, 2,6-difluorophenyl, 2-chloro-6-methylphenyl, 2,4,6-trichlorophenyl, 2,6-dimethoxyphenyl, 4-(diethylaminoethoxy)phenyl, 2-fluoro-3,5-dimethoxyphenyl, 2,6-dibromophenyl, 2,6-dinitrophenyl, 2,6-di-(trifluoromethyl)phenyl, 3-(dimethylaminoethyl) phenyl, 2,6-dimethylphenyl, 2,3,6-trimethylphenyl, 2,6-dibromo-4-methylphenyl, and the like.

The process of this invention is carried out by reacting the 2-(4-imino-4H-pyridin-1-yl)-pyrido[2,3-d]pyrimidine of Formula L, preferably as an acid addition salt such as the hydrochloride salt, with a 4-aminopyridine in the presence of a base and in an organic solvent to provide the corresponding 2-(pyridin-4-yl-amino)-pyrido[2,3-d]pyrimidine of Formula II. The reaction occurs as shown below:

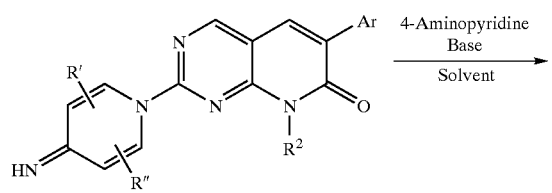

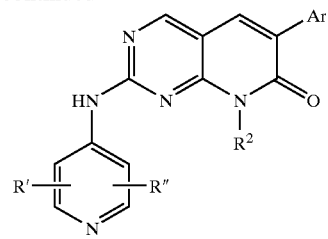

The 4-aminopyridine used in the process has the formula

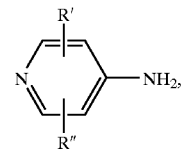

wherein R' and R" are the same substituents on the 4-imino-1,4-dihydropyridine ring portion of the starting material. The starting pyridopyrimidine of Formula I and the base typically are used in approximately equimolar amounts, whereas the 4-aminopyridine generally is used in only a catalytic amount, for example from about 0.05 to about 0.5 equivalents relative to the pyridopyrimidine starting material.

"Base" as used herein means any inorganic compound that provides negative ions in solutions of water or polar organic solvents. Typical bases include inorganic carbonates and bicarbonates such as potassium carbonate, sodium bicarbonate, potassium bicarbonate, and sodium bicarbonate. Hydroxides such as sodium hydroxide and potassium hydroxide also can be used.

The process of this invention is generally carried out in an unreactive organic solvent. The particular solvent is not critical. Typical solvents commonly used include dimethylsulfoxide, dimethylformamide, acetonitrile, tetrahydrofuran, glyme, diglyme, sulfolane, and N-methylpyrrolidinone (NMP).

The reaction generally is substantially complete within about 24 hours to about 60 hours when carried out at a temperature of about 30° C. to about 190° C. While the exact temperature at which the reaction is conducted is not critical, heating above room temperature is generally preferred in order to promote substantially complete conversion within the above noted time ranges.

The process proceeds through a dimer-like compound of the Formula III

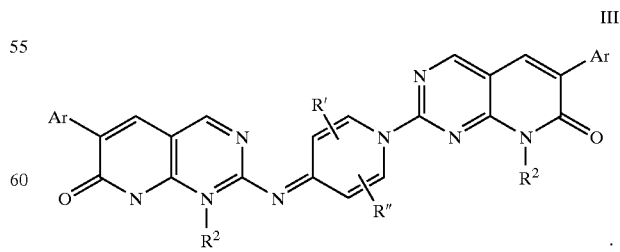

This dimer-like compound is produced within about 1 hour to about 3 hours upon mixing the imine of Formula I with an aminopyridine of the formula

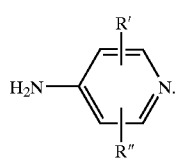

However, continued stirring, especially at elevated temperatures of about 60° C. to about 100° C., results in complete conversion of the dimer-like compound to the desired compound of Formula II. The dimer-like compound of Formula III generally is reacted with an aminopyridine in situ, thus avoiding isolation. The compound can be isolated, however, if desired.

The final product of the process, a compound of Formula II, is readily isolated by simply filtering the reaction mixture and washing the precipitate with a solvent such as water, or an acid such as 6N hydrochloric acid followed by a wash with an organic solvent such as acetonitrile or methanol. Alternatively, the reaction mixture can first be concentrated, for example by evaporation of the reaction solvent under reduced pressure, and the mixture can be suspended in a solvent such as ethyl acetate or ethanol, filtered, and again washed with water, or a weak acid, followed by a wash with an organic solvent. The solid product generally is dried in a vacuum oven at about 30° C. to about 50° C.

If desired, the product of Formula II can be further purified by routine processes such as chromatography, recrystallization from solvents such as DMSO, or it can be converted to a pharmaceutically acceptable acid addition salt.

Pharmaceutically acceptable acid addition salts of the compound of Formula II include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fulmarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J of Pharmaceutical Science*, 1977; 66: 1–19).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise, the salts are equivalent to their respective free base for purposes of the present invention.

The starting material required for the present process is a 2-(4-imino-4H-pyridin-1-yl)-pyrido[2,3-d]pyrimidine of Formula I. This starting material can be prepared by reacting a 2-alkylsulfinyl-pyrido[2,3-d]pyrimidine with a 4-aminopyridine. The 2-alkylsulfinyl compound is available as described in U.S. Pat. No. 5,733,914. The 2-alkylsulfinyl-pyrido[2,3-d]pyrimidine is reacted with an equimolar or excess of 4-aminopyridine, generally as an acid addition salt, as follows:

Formula I

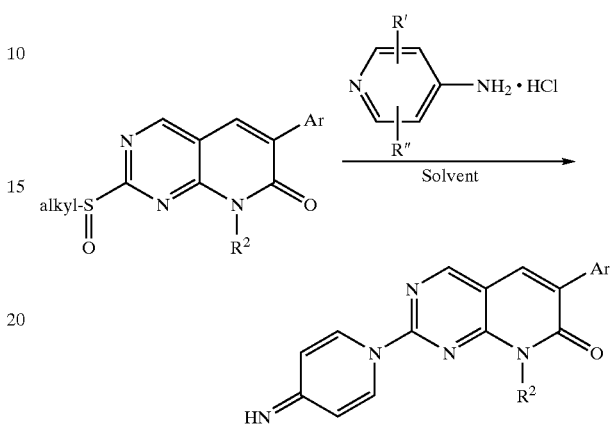

The reaction generally is carried out in an organic solvent such as acetonitrile, tetrahydrofuran, or the like, and generally is substantially complete within about 2 to 10 hours when carried out at an elevated temperature of about 30° C. to about 80° C. The product of Formula I is readily isolated as an acid addition salt by simply filtering the reaction mixture and drying it, either in an oven or in open air.

As noted above, the 2-alkylsulfinyl-pyrido[2,3-d]pyrimidines are available by the process described in U.S. Pat. No. 5,733,914. That process comprises reacting an aryl acetonitrile with a 2-alkylsulfanyl-4-alkylamino-pyrimidine-5-carboxaldehyde to produce the corresponding 2-alkylsulfanyl-pyrido[2,3-d]pyrimidine, followed by oxidation to the sulfoxide (a 2-alkylsulfinyl-pyrido[2,3-d]pyrimidine). A further embodiment of this invention is an improved process for making the initial 2-alkylsulfanyl intermediate that comprises reacting an arylacetic acid ester (instead of an aryl acetonitrile) with a 2-alkylsulfanyl-4-alkylamino-pyrimidine-5-carboxaldehyde. The reactants are generally mixed in approximately equimolar quantities in an unreactive organic solvent and in the presence of a coupling reagent such as 1,8-diazabicyclo[5.4.0]undec-7-ene. The reaction is generally complete within about 1 to 8 hours when carried out at an elevated temperature of above 40° C. to about 100° C. The product, 2-alkylsulfanyl pyridopyrimidine, is readily isolated by filtration. This process affords surprisingly better yields and improved purity compared to that described in U.S. Pat. No. 5,733,914. The 2-alkylsulfanyl pyridopyrimidine is readily oxidized to the corresponding 2-alkylsulfinyl derivative by reaction with normal oxidation agents such as m-chloroperbenzoic acid or trans-2-phenylsulfonyl-3-phenyl-oxaziridine.

The following detailed examples further illustrate the process of this invention. The examples are provided as illustration only, and are not intended to limit the invention in any respect.

PREPARATION 1

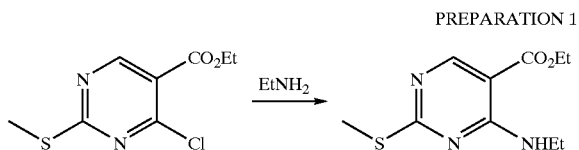

4-Ethylamino-2-methylsulfanyl-pyrimidine-5-carboxylic acid ethyl ester

A 22-L, 4-necked round-bottomed flask was equipped with a mechanical stirrer, a dropping funnel, and a thermometer. The flask was charged with the ethyl 4-chloro-2-(methylthio)-5-pyrimidinecarboxylate (1.53 kg, 6.56 mol), triethylamine (2.74 L, 19.7 mol, 3 eq), and 7.5 L of tetrahydrofuran to give a solution. The aqueous ethylamine (0.53 L, 6.56 mol, 1 eq) was added via the dropping funnel over 20 minutes. The reaction temperature rose to 35° C. during the addition. The reaction was stirred at ambient temperature for 2 hours. The reaction was checked for completion using TLC ($SiO_2$; 7:3/heptane:ethyl acetate). The precipitate (triethylamine hydrochloride) was filtered off and washed 2 times with tetrahydrofuran, combining the washes with the original filtrate. The tetrahydrofuran was stripped to near dryness on a rotary evaporator. The residue was partitioned between saturated aqueous sodium bicarbonate (500 mL) and ethyl acetate (1 L). Note that there is carbon dioxide gas evolution from the bicarbonate both during the partitioning and the subsequent washes. The layers were separated and the organic layer washed 2 times with saturated aqueous sodium bicarbonate and 1 time with brine. The solution was dried over magnesium sulfate, filtered, and stripped to give the titled compound as an off-white solid. Yield: 95%.

PREPARATION 2

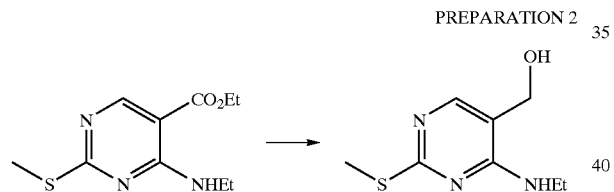

4-Ethylamino-2-methylsulfanyl-pyrimidin-5-yl)-methanol

The 50-L built-in reactor was purged with argon 3 times, and then a positive argon pressure was maintained throughout the process. The reactor was charged with 4 L of tetrahydrofuran, followed by lithium aluminum hydride (1 M in tetrahydrofuran, 6.77 kg, 7.48 L, 7.48 mol, 1.2 eq). The chiller/heater was set to 18° C. and activated. The product of Preparation 1, 4-ethylamino-2-methylsulfanyl-pyrimidine-5-carboxylic acid ethyl ester (1.5 kg, 6.23 mol, 1 eq), was dissolved in 11 L of tetrahydrofuran (0.58 M) and was added to the reaction vessel using a pump over ~2 hours. TLC ($SiO_2$; 7:3/heptane:ethyl acetate) was used to monitor the reaction for completion. When the reaction was complete, the chiller/heater was set to 10° C. The excess hydride was quenched by adding successively: 1.25 L of water, 1.25 L of 15 wt % sodium hydroxide, and then 4.1 L of water. The first portion of water was added quite slowly and with vigorous stirring to keep down the foaming and to keep the temperature below 30° C. As the quench continues, the addition rate was gradually increased until the final portion of water could be added in a steady stream. The reaction mixture was then stirred for 1 hour before filtering through a 1-inch plug of celite in a 2 L coarse fritted funnel. The salts were washed once with tetrahydrofuran on the funnel. The tetrahydrofuran was stripped, then the residue azeotroped 2 times with 1 L portions of toluene. The resulting solid was washed from the flask using heptane, then dried in a vacuum oven at 40° C. to give the titled compound which is used in the next step without further purification.

PREPARATION 3

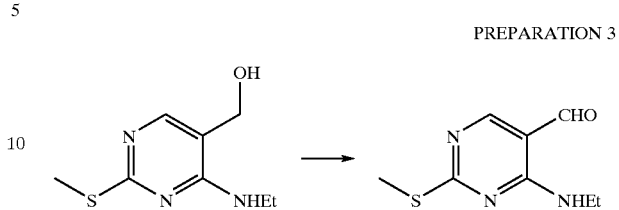

4-Ethylamino-2-methylsulfanyl-pyrimidine-5-carboxaldehyde

A 50-L round-bottomed flask equipped with a mechanical stirrer was charged with 565 g (2.84 mol) of the product of Preparation 2, 4-ethylamino-2-methylsulfanyl-pyrimidin-5-yl)-methanol, 1.23 kg (14.2 mol, 5 eq) of manganese (IV) oxide, and 19 L of chloroform. The mixture was stirred 24 hours at room temperature, then checked by TLC ($SiO_2$; 7:3/heptane:ethyl acetate) for completion of reaction. The reaction was filtered through a plug of celite and the chloroform stripped to give the titled compound in 90% yield.

EXAMPLE 1

2-Methylsulfanyl-6-(3, 5-dimethoxyphenyl)-8-ethyl-8H-pyrido[2,3-d]pyrimidine-7-one

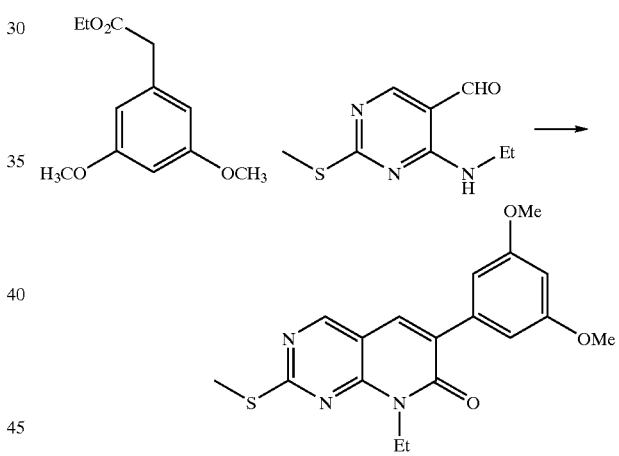

A 5-L round bottomed flask was charged with 516 g (2.62 mol) of 4-ethylamino-2-methylsulfanyl-pyrimidine-5-carboxaldehyde, 587 g (2.62 mol) of (3,5-dimethoxyphenyl)-acetic acid ethyl ester, and 391 mL (2.62 mol) of 1,8-diazabicyclo[5.4.0]undec-7-ene. The mixture was heated at 80° C. for one hour. Thin layer chromatography (TLC) (silica, 6:4/heptane:ethyl acetate, developed in an iodine chamber) showed all the 4-ethylamino-2-methylsulfanyl-pyrimidine-5-carbaldehyde was consumed. Ethyl alcohol (absolute, 2.75 L) was added to the reaction vessel, and the reaction mixture was cooled to room temperature. The solid that precipitated was collected by filtration, washed once with ethyl alcohol, and dried in a vacuum oven at 45° C. for 12 hours to provide 530 g (57% yield) of 2-methylsulfanyl-6-(3,5-dimethoxyphenyl)-8-ethyl-8H-pyrido[2,3-d]pyrimidine-7-one. Proton NMR (DMSO) is consistent with the structure: $^1$H NMR (DMSO): δ 8.86 (s, 1H), 8.10 (s, 1H), 6.83 (d, 2H), 6.51 (s, 1H), 4.36 (q, 2H), 3.75 (s, 1H), 2.58 (s, 3H), 1.22 (t, 3H). The combined mother liquor and washes were allowed to stand at room temperature for seven days. At this time a second crop of precipitate was collected, washed once with ethyl alcohol, and dried in a vacuum oven at 45° C. for 12 hours to provide 79 g (8.5% yield) of 2-methylsulfanyl-6-(3,5-dimethoxyphenyl)-8-ethyl-8H-pyrido[2,3-d]pyrimidine-7-one. Proton NMR (DMSO) is consistent with the structure.

EXAMPLE 1A
2-(Methylsulfanyl)-6-(3,5-dimethoxyphenyl)-8-ethyl-8H-pyrido[2,3-d]-pyrimidine-7-one 4.8 kg of 4-ethylamino-2-methylsulfanyl-pyrimidine-5-carboxaldehyde and 5.5 kg of (3,5-dimethoxyphenyl)-acetic acid ethyl ester were dissolved in 10 L of DMSO at room temperature and stirred. 4.4 kg of 1,8-diazabicyclo[5.4.0]undec-7-ene was added to the reaction mixture. The mixture was heated at about 45–50° C. for at least 3 hours. The reaction was monitored by reverse-phase HPLC (YMC-AQ column, 60:40 $CH_3CN$/0.02 M SDS, pH 2.2, 1.0 mL/min, 254 nm). When the reaction was completed, ethyl alcohol (3 L) was added to the reaction vessel, which was cooled to 5–15° C. The yellow product was precipitated and collected by filtration, washed with a mixture of isopropyl alcohol and water (3 L+3 L), and dried in a vacuum tray dryer at about 40–45° C. for at least 12 hours using a house vacuum (~30 in Hg) to provide 7.3 kg (84% yield) of 2-(methylsulfanyl)-6-(3,5-dimethoxyphenyl)-8-ethyl-8H-pyrido[2,3-d]pyrimidine-7-one. Proton NMR is consistent with the structure.

EXAMPLE 2
2-Methylsulfinyl-6-(3,5-dimethoxy-phenyl)-8-ethyl-8H-pyrido[2,3-d]pyrimidin-7-one To a solution of 2-methylsulfanyl-6-(3,5-dimethoxy-phenyl)-8-ethyl-8H-pyrido[2,3-d]pyrimidin-7-one (17.0 g, 0.048 mol) in $CHCl_3$ (150 mL), was added trans-2-phenylsulfonyl-3-phenyloxaziridine (15.2 g, 0.058 mol; Organic *Synthesis*, 1987; 66: 203–210). The reaction mixture was stirred overnight at room temperature. The product was purified by filtering through a large sintered glass funnel filled with silica gel wetted with $CHCl_3$. The product was eluted off the silica gel with the following order of solvents: $CHCl_3$, EtOAc, MeOH/$CHCl_3$ (1:20), and MeOH/$CHCl_3$ (1:10). The solvent was removed under reduced pressure and the residue taken up in hot EtOAc (40 mL, 50° C.), filtered, and concentrated to 20 mL by evaporation under reduced pressure. The product precipitated and was collected by filtration to give 13.77 g of the titled compound, mp 114–116° C.

Alternatively, To a solution of the product of Example 1 or 1A, (536.2 g, 1.50 mol) in $CHCl_3$ (3.4 L), was added trans-2-phenylsulfonyl-3-phenyloxaziridine (431 g, 1.65 mol; Organic *Synthesis*, 1987; 66:203–210). The reaction mixture was stirred overnight at room temperature. Methyl t-Butyl Ether mTBE) was added to the solution until a precipitate formed (~7 L). The solid was collected by filtration, washed once with MTBE and dried in a vacuum oven at room temperature. Proton NMR (DMSO) is consistent with the structure.

EXAMPLE 3
2-(4-Imino-4H-pyridin-1-yl)-6-(3,5-dimethoxyphenyl)-8-ethyl-8H-pyrido[2,3-d]pyrimidin-7-one hydrochloride To a solution of 220 g (0.59 mol) of the product of Example 2, 2-methylsulfinyl-6-(3,5-dimethoxy-phenyl)8-ethyl-8H-pyrido[2,3-d]pyrimidine-7-one, in 2 L of acetonitrile was added a solution of 100 g (0.765 mol, 1.3 eq) of 4-aminopyridine hydrochloride in 700 mL of ethanol. The mixture was heated to 40° C. and stirred for 6 hours. The mixture was then cooled to 24° C. and filtered to provide 256 g (99%) of 2-(4-imino-4H-pyridin-1-yl)-6-(3,5-dimethoxyphenyl)-8-ethyl-8H-pyrido[2,3-d]-pyrimidin-7-one hydrochloride; mp 295–300° C. (dec).

EXAMPLE 4
2-(Pyridin-4-ylamino)-6-(3,5-dimethoxyphenyl)-8-ethyl-8H-pyrido[2,3-d]-pyrimidin-7-one To a stirred solution of 330 g (0.75 mol) of 2-(4-imino-4H-pyridin-1-yl)-6-(3,5-dimethoxyphenyl)-8-ethyl-8H-pyrido[2,3-d]pyrimidin-7-one hydrochloride in 1.5 L of dimethylsulfoxide were added in one portion 114 g (0.825 mol) of powdered potassium carbonate, followed by the addition of a solution of 2.8 g (0.03 mol; 0.05 eq) 4-aminopyridine in 50 mL of dimethylsulfoxide. The reaction mixture was heated to 100° C., and aliquots were removed after 1 hour and analyzed by reverse phase high pressure liquid chromatography (RP-HPLC) (YMC-AQ column, 60:40 $CH_3CN$/0.02 M SDS, pH 2.2, 1.0 mL/min, 254 nm). After 40 minutes, the reaction was shown to produce the title compound, plus a dimer-like compound of the formula

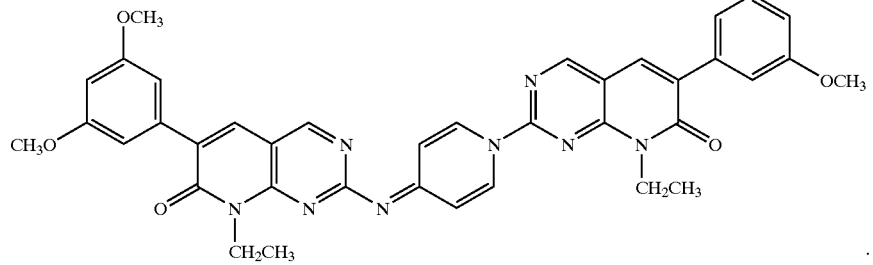

The foregoing dimer-like compound is named 2-{4-(6-[3,5-dimethoxyphenyl-7-oxo-8-ethyl-8H-pyrido[2, 3-d]pyrimidine-2-yl]-imino)-4H-pyridin-1-yl}-6-(3,5-dimethoxyphenyl)-8-ethyl-8H-pyrido[2,3-d]pyrimidine-7-one.

The reaction mixture was stirred at 100° C. for a total of 60 hours, at which time RP-HPLC revealed that all dimers had been converted to 2-(pyridin-4-ylamino)-6-(3,5-dimethoxyphenyl)-8-ethyl-8H-pyrido[2,3-d]pyrimidin-7-one. The reaction mixture was cooled to 45° C. and acidified by addition of 300 mL of 6N hydrochloric acid (the acidification was exothermic). The acidic solution was stirred for 4 hours at 24° C., during which time the product had precipitated as a bright yellow solid. The precipitate was filtered and washed with 200 mL of 6N hydrochloric acid, with 250 mL of water, with 800 mL of acetonitrile, and finally with 300 mL of methyl tert-butyl ether. The precipitate was dried in a vacuum oven at 40° C. for 12 hours to provide 303 g (92% yield) of 2-(pyridin-4-ylamino)-6-(3,5-dimethoxyphenyl)-8-ethyl-8H-pyrido[2,3-d]pyrimidin-7-one hydrochloride; mp 295–300° C. (dec). Mass Spec (APCI) 439.89 m/z.

The hydrochloride salt was reacted with 1N sodium hydroxide to provide 2-(pyridin-4-ylamino)-6-(3,5-dimethoxyphenyl)-8-ethyl-8H-pyrido[2,3-d]pyrimidine-7-one free base: mp 305–307° C. Mass Spec (APCI) 403.9 m/z.

What is claimed is:

1. A process for preparing a 2-(pyridin-4-ylamino)-pyrido[2,3-d]pyrimidine of Formula II

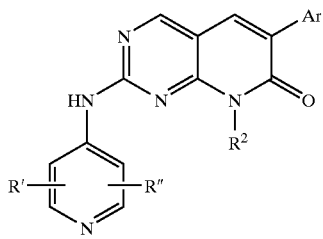

comprising reacting a 4-aminopyridine of the formula

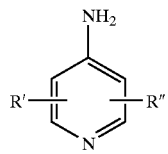

with a 2-(4-imino-4H-pyridin-1-yl)-pyrido[2,3-d]pyrimidine of Formula I

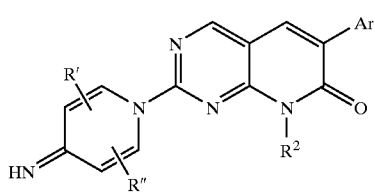

in the presence of a base: wherein
   R' and R" independently are hydrogen, $C_1$–$C_6$ alkyl, $C_1$–$C_6$ alkoxy, or phenyl;
   $R^2$ is $(CH_2)_n$Ph, where Ph is phenyl or substituted phenyl, and n is 0, 1, 2, or 3; heteroaromatic; cycloalkyl; $C_1$–$C_6$ alkyl; or $C_2$–$C_6$ alkenyl; where the alkyl and alkenyl groups may be substituted by $NR_5R_6$, phenyl, substituted phenyl, or cycloalkyl, and
   where $R_5$ and $R_6$ are independently $C_1$–$C_6$ alkyl; $C_2$–$C_6$ alkenyl; $(CH_2)_n$Ph where Ph is phenyl or substituted phenyl, and n is 0, 1, 2, or 3; cycloalkyl; or heteroaromatic, or $R_5$ and $R_6$ taken together with the nitrogen to which they are attached can complete a nitrogen containing ring having 3 to 7 carbon atoms and optionally containing 1 or 2 additional heteroatoms selected from the group consisting of nitrogen, substituted nitrogen, oxygen, and sulfur; and Ar is phenyl, substituted phenyl, or heteroaromatic.

2. A process according to claim 1 wherein Ar is substituted phenyl.

3. A process according to claim 1 wherein Ar is di–$C_1$–$C_6$ alkoxy phenyl.

4. A process according to claim 1 wherein $R^2$ is $C_1$–$C_6$ alkyl.

5. A process according to claim 1 wherein R' and R" both are hydrogen.

6. A process for preparing a compound of the formula

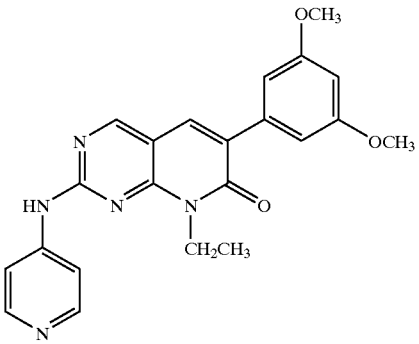

comprising reacting 4-aminopyridine with a compound of the formula

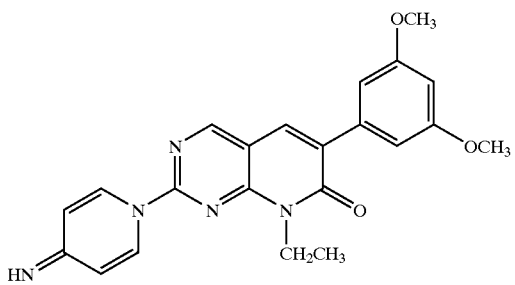

in the presence of a base.

7. A compound of the Formula I

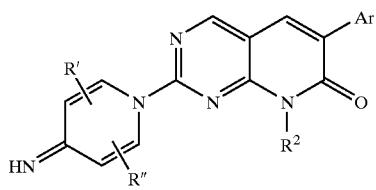

wherein:
   Ar is phenyl, substituted phenyl, or heteroaromatic;
   R' and R" independently are hydrogen, $C_1$–$C_6$ alkyl, $C_1$–$C_6$ alkoxy, or phenyl; and $R^2$ is $(CH_2)_n$Ph, where Ph is phenyl or substituted phenyl, and n is 0, 1, 2, or 3; heteroaromatic; cycloalkyl; $C_1$–$C_6$ alkyl; or $C_2$–$C_6$ alkenyl, where the alkyl and alkenyl groups may be substituted by $NR_5R_6$, phenyl, substituted phenyl, or cycloalkyl, and
   where $R_5$ and $R_6$ are independently $C_1$–$C_6$ alkyl; $C_2$–$C_6$ alkenyl; $(CH_2)_n$Ph where Ph is phenyl or substituted phenyl, and n is 0, 1, 2, or 3; cycloalkyl; heteroaromatic; or $R_5$ and $R_6$ taken together with the nitrogen to which they are attached can complete a nitrogen-containing ring having 3 to 7 carbon atoms and optionally containing 1 or 2 additional heteroatoms selected from the group consisting of nitrogen, substituted nitrogen, oxygen, and sulfur.

8. A process for preparing a compound of Formula II

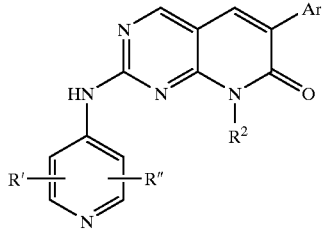

wherein:

Ar is phenyl, substituted phenyl, or heteroaromatic;

R' and R" independently are hydrogen, $C_1$–$C_6$ alkyl, $C_1$–$C_6$ alkoxy, or phenyl; and $R^2$ is $(CH_2)_n$Ph, where Ph is phenyl or substituted phenyl, and n is 0, 1, 2, or 3; heteroaromatic; cycloalkyl; $C_1$–$C_6$ alkyl; or $C_2$–$C_6$ alkenyl, where the alkyl and alkenyl groups may be substituted by $NR_5R_6$; phenyl; substituted phenyl; cycloalkyl; and where $R_5$ and $R_6$ are independently $C_1$–$C_6$ alkyl; $C_2$–$C_6$ alkenyl; $(CH_2)_n$Ph where Ph is phenyl or substituted phenyl, and n is 0, 1, 2, or 3; cycloalkyl; or heteroaromatic; or $R_5$ and $R_6$ taken together with the nitrogen to which they are attached can complete a nitrogen containing ring having 3 to 7 carbon atoms and optionally containing 1 or 2 additional heteroatoms selected from the group consisting of nitrogen, substituted nitrogen, oxygen, and sulfur comprising reacting an aminopyridine of formula

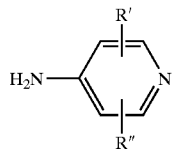

with a compound of Formula III

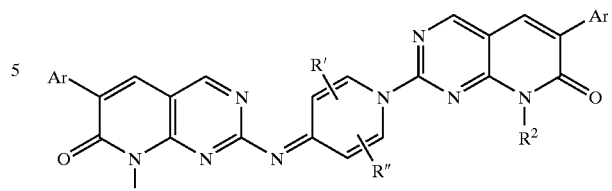

in an unreactive organic solvent.

9. A compound of Formula III

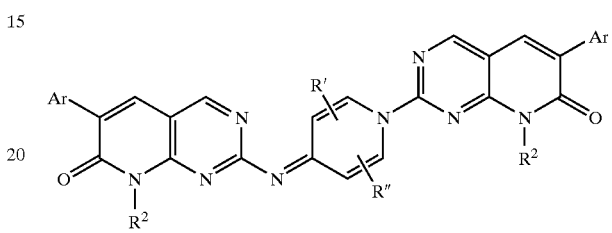

wherein:

Ar is phenyl, substituted phenyl, or heteroaromatic;

R' and R" independently are hydrogen, $C_1$–$C_6$ alkyl, $C_1$–$C_6$ alkoxy, or phenyl; and $R^2$ is hydrogen; $(CH_2)_n$Ph, where Ph is phenyl or substituted phenyl, and n is 0, 1, 2, or 3; heteroaromatic; cycloalkyl; $C_1$–$C_6$ alkyl; or $C_2$–$C_6$ alkenyl; where the alkyl and alkenyl groups may be substituted by $NR_5R_6$, phenyl, substituted phenyl, or cycloalkyl, and where $R_5$ and $R_6$ are independently $C_1$–$C_6$ alkyl; $C_2$–$C_6$ alkenyl; $(CH_2)_n$Ph where Ph is phenyl or substituted phenyl, and n is 0, 1, 2, or 3; cycloalkyl; or heteroaromatic; or $R_5$ and $R_6$ taken together with the nitrogen to which they are attached can complete a nitrogen containing ring having 3 to 7 carbon atoms and optionally containing 1 or 2 additional heteroatoms selected from the group consisting of nitrogen, substituted nitrogen, oxygen, and sulfur.

\* \* \* \* \*